United States Patent [19]

Isshiki et al.

[11] 4,212,989
[45] Jul. 15, 1980

[54] PROCESS FOR PRODUCING CARBOXYLIC ACIDS OR ESTERS THEREOF

[75] Inventors: Tomiya Isshiki, Tokyo; Yasuhiko Kijima; Yuh Miyauchi, both of Matsudo, all of Japan

[73] Assignee: Mitsubishi Gas Chemical Company, Inc., Tokyo, Japan

[21] Appl. No.: 955,411

[22] Filed: Oct. 26, 1978

[30] Foreign Application Priority Data

Nov. 1, 1977 [JP] Japan ................................. 52-131140

[51] Int. Cl.$^2$ ........................ C07C 67/36; C07C 67/37
[52] U.S. Cl. .................................... 560/232; 560/114; 560/130; 560/180; 560/204; 562/406; 562/497; 562/517; 562/519
[58] Field of Search ............... 560/130, 232, 114, 204, 560/180; 562/517, 519, 497, 406

[56] References Cited

U.S. PATENT DOCUMENTS

| 3,769,329 | 10/1973 | Paulik et al. | 562/519 |
| 3,813,428 | 5/1974 | Paulik et al. | 562/519 |

FOREIGN PATENT DOCUMENTS

| 921938 | 11/1954 | Fed. Rep. of Germany . |
| 933148 | 8/1955 | Fed. Rep. of Germany . |
| 947469 | 7/1956 | Fed. Rep. of Germany . |
| 47-3331 | 1/1972 | Japan . |

Primary Examiner—Jane S. Myers
Attorney, Agent, or Firm—Wenderoth, Lind & Ponack

[57] ABSTRACT

In a process for producing a carboxylic acid or its ester by reacting an alcohol or an ether with carbon monoxide, the improvement wherein the reaction is performed in the presence of, as a solvent, an aryl ester of an aliphatic carboxylic acid represented by the formula

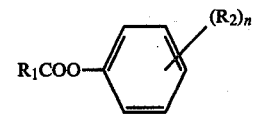

wherein n is an integer of 1 to 5, $R_1$ represents hydrogen or $C_1$–$C_4$ alkyl or alkenyl, and $R_2$ represents hydrogen, alkyl, aryl, alkenyl, hydroxymethyl, acyl, acyloxy, formyl, carboxy, hydroxy, halogen, sulfo, nitro, nitroso, amino, acid amide or cyano, and two or more $R_2$ groups may be the same or different, and the substituents $R_2$ may be bonded to each other to form a penta- or hexacarbocyclic or heterocyclic ring.

2 Claims, No Drawings

PROCESS FOR PRODUCING CARBOXYLIC ACIDS OR ESTERS THEREOF

This invention relates to a process for producing carboxylic acids and/or their esters by reacting alcohols or ethers with carbon monoxide.

A typical known method for producing carboxylic acids by the carbonylation of alcohols is the production of acetic acid from methanol and carbon monoxide. For example, U.S. Pat. Nos. 2,729,651 and 2,727,902 and German Pat. Nos. 921,938, 933,148 and 947,469 disclose a so-called Reppe method which comprises reacting alcohols, ethers or esters with carbon monoxide using a transition metal such as iron, cobalt or nickel and a compound of halogen such as iodine or bromine as a catalyst.

These methods, however, require severe conditions involving high temperatures and pressures, and many of them do not give enough yields. In an attempt to overcome these disadvantages, methods have recently been developed which comprise the use of a complex of a platinum-group metal typified by rhodium as a catalyst (Japanese Patent Publications Nos. 3331/1972 to 3337/1972 which correspond to U.S. patent applications Ser. Nos. 701,637 to 701,639, 628,577, 628,578, 628,581 and 628,591). These methods which are catalyzed by platinum-group metal complexes can effect carbonylation under milder conditions than the Reppe method, and can give better yields with lesser amounts of by-products. However, in these methods, water, hydrogen halide, etc. form by various side-reactions which occur during the reaction, and particularly, when an ester is used as a starting material, the pressure of water in the reaction system is essential. The presence of such substances in the reaction system leads to the formation of a corrosive atmosphere. This poses a problem of the quality of the reactor material, and an extra operation of separating the resulting carboxylic acid from water is required.

It is an object of this invention therefore to provide a process for producing carboxylic acids or their esters which removes these defects of the prior art, and does not give rise to the formation of water and hydrogen halide as by-products.

The above object can be achieved by an improved process for producing a carboxylic acid or its ester by reacting an alcohol or an ether with carbon monoxide, wherein the improvement comprises effecting the reaction in the presence of, as a solvent, an aryl ester of an aliphatic carboxylic acid represented by the formula

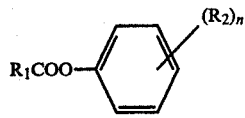 (I)

wherein n is an integer of 1 to 5, $R_1$ represents hydrogen or $C_1$–$C_4$ alkyl or alkenyl, and $R_2$ represents hydrogen, alkyl, aryl, alkenyl, hydroxymethyl, acyl, acyloxy, formyl, carboxy, hydroxy, halogen, sulfo, nitro, nitroso, amino, acid amide or cyano, and two or more $R_2$ groups may be the same or different, and the substituents $R_2$ may be bonded to each other to form a penta- or hexacarboxylic or heterocyclic ring.

The alcohols and ethers used as starting materials in this invention include aliphatic alcohols containing 1 to 20 carbon atoms, aliphatic ethers containing 2 to 30 carbon atoms, aromatic alcohols containing 7 to 20 carbon atoms and aromatic ethers containing 7 to 30 carbon atoms. Examples of these alcohols and ethers are methanol, ethanol, propanol, butanol, pentanol, hexanol, heptanol, decanol, ethylene glycol, propylene glycol, butanediol, hexanediol, cyclohexanol, benzyl alcohol, phenylethanol, dimethyl ether, diethyl ether, dipropyl ether, dibutyl ether, methyl ethyl ether, cyclohexyl methyl ether, anisole, phenetole, methylbenzyl ether, methyl cellosolve, butyl cellosolve, monoglyme and diglyme.

The reaction can be conveniently carried out in this invention by using at least one metal of Group VIII of the periodic table as a main catalyst and at least one iodine-containing substance selected from iodine and iodine compounds as a promotor. The metals of Group VIII of the periodic table are iron, nickel, cobalt, ruthenium, rhodium, palladium, osmium, iridium and platinum. Compounds of these metals of optional atomic valences can be used. Examples include iron iodide, iron carbonyl, cobalt iodide, cobalt carbonyl, nickel acetate, nickel powder, nickel acetylacetonate, $RhCl_3$, $[RhI(CO)_2]_2$, $RhBr(P\phi_3)_3$, $Rh(CO)_3$, $[Rh(CH_3COO)_2]_2$, $IrCl_3$, $Ir_2(CO)_4I_2$, $Ir_2(CO)_8$, $Ir(SnCl_3)(P\phi_3)_3$, $IrI(CO)(Sb\phi_3)_2$, $PdI_2$, $[Pd(P\phi_3)_2]Cl_2$, $Pd[(n-C_4H_9)_3P](CO)Cl_2$, $RuBr_3$, $Ru(CO)_{12}$, $RuI_2(CO)(As\phi_3)_3$, $H_2PtCl_6$, $Pt(As\phi_3)_2$, $Os(CO)_5$, and $OsBr_3(As\phi_3)_3$. $\phi$ represents a phenyl group.

Iodine and all iodine-containing compounds can be used as the promotor.

Examples of especially suitable promotors are as follows:

$$RI_n \qquad (II)$$

wherein R represents hydrogen or alkyl, and n is 1 to 3, $$I_2 \text{ or } I_3^- \qquad (III)$$

$$RCOI \qquad (IV)$$

wherein R is alkyl, $$MI_n \qquad (V)$$

wherein M is an alkali or alkaline earth metal, and n is 1 or 2, $$R_4MI, R_4MI_3, \text{ or } R_3MI_2 \qquad (VI)$$

wherein R is hydrogen, alkyl or aryl, and M is a nitrogen, phosphorus, arsenic or antimony atom.

Examples of suitable iodine-containing compounds as promotors are $I_2$, $KI_3$, HI, $CH_3I$, $C_2H_5I$, $C_3H_7I$, $C_4H_9I$, $CH_2I_2$, $C_2H_4I_2$, $CHI_3$, $CH_3COI$, $C_2H_5COI$, NaI, KI, LiI, and $CaI_2$.

In the present invention, the reaction can be performed by using a combination of the main catalyst and the promotor exemplified hereinabove. To quicken the rate of the reaction, an organic accelerating agent can be added. Suitable organic accelerating agents are compounds capable of forming coordination compounds with metals of Group VIII of the periodic table to form a coordination bond in the molecular structure. A wide range of organic compounds of trivalent nitrogen, phosphorus, arsenic or antimony can be used.

Examples of useful organic nitrogen compounds include organic nitrogen compounds of the formula

  (VII)

wherein $R_1$, $R_2$ and $R_3$ are the same or different and represent hydrogen, alkyl or aryl,
such as trimethylamine, diethylamine, methyldiethylamine, tributylamine, aniline and N,N-dimethylaniline; organic nitrogen compounds of the formula

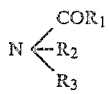  (VIII)

wherein $R_1$, $R_2$ and $R_3$ are the same or different and each represent hydrogen, alkyl or aryl,
such as N,N-dimethyl acetamide and N-methyl-N-phenyl acetamide; heterocyclic nitrogen compounds such as pyridine, hydroxyquinoline and imidazole; nitriles such as acetonitrile, propionitrile, adiponitrile and benzonitrile; and ammonium salts such as ammonium acetate.

Examples of compounds of phosphorus, arsenic or antimony are compounds resulting from replacing N of the compounds of formula (VII) by P, As or Sb, such as trimethylphosphine, tributylphosphine, diphenylphosphine, triphenylphosphine, methyldiphenylphosphine, triphenylarsine and triphenylstibine.

The amount of the group VIII metal used as a main catalyst in this invention is generally $10^{-6}$ to 1 mole, preferably $10^{-4}$ to $10^{-1}$ mole, per liter of the starting materials and solvent combined. The amount of the iodine-containing substance used as a promotor is generally $10^{-6}$ to 20 moles, preferably $10^{-4}$ to 10 moles, as iodine atom, per liter of the starting materials and solvent combined. The amount of the nitrogen-group element compound required to form a stoichiometric coordination compound with the group VIII metal is generally $10^{-6}$ to 10 moles, preferably $10^{-4}$ to 5 moles, per liter of the starting materials and solvent combined.

In the present invention, the aryl ester of an aliphatic carboxylic acid expressed by formula (I) is used as a reaction solvent. Specific examples of the solvent include phenyl formate, phenyl acetate, phenyl propionate, phenyl butyrate, phenyl valerate, tolyl acetate, xylyl acetate, mesityl acetate, cumenyl acetate, ethyl phenyl acetate, propyl phenyl acetate, butyl phenyl acetate, chlorophenyl acetate, nitrophenyl acetate, nitrosophenyl acetate, aminophenyl acetate, cyanophenyl acetate,

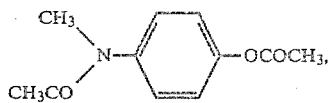

diacetoxybenzene, naphthyl acetate, naphthyl propionate, naphthyl butyrate, diacetoxynaphthalene, diacetoxyanthracene, (diacetoxy)methylanthracene, (diacetoxy)ethylanthracene and (diacetoxy)amylanthracene. The solvent specifically used in this invention serves to substantially inhibit the formation of hydrogen iodide and water and exclude these substances from the reaction system.

If desired, the solvent may be used in conjunction with another solvent having compatibility with it. Examples of other solvents that can generally be used include organic acids such as acetic acid, propionic acid, butyric acid, octanoic acid, phthalic acid, benzoic acid and cyclohexanecarboxylic acid, hydrocarbons such as dodecane, hexadecane, benzene, naphthalene and biphenyl, and inorganic acid esters such as triphenyl phosphate, tricresyl phosphate, dibutyl phosphate, dibutylphenyl phosphate, tetramethyl ortho-silicate, and tetrabutyl silicate.

The amount of the aryl ester of aliphatic carboxylic acid ester having formula (I) can be varied over a wide range. It is generally at least 0.5 mole, preferably at least 1 mole, as phenoxy groups per mole of the alkyl groups of the starting alcohol or ether.

Preferably, the reaction for the practice of the process of this invention can be performed at a temperature of 50° to 300° C., especially 100° to 240° C., and a pressure of 0 to 1,000 kg/cm².G, especially 2 to 200 kg/cm².G. (as a partial pressure of carbon monoxide). Carbon monoxide used needs not to be of high purity, and may contain hydrogen, carbon dioxide, methane, nitrogen, rare gases, water, etc. Carbon monoxide of extremely low purity is not desired because it will increase the pressure of the reaction system.

The process of this invention can afford carboxylic acids or their esters by carbonylation of the corresponding alcohols or ethers without forming corrosive substances such as water and hydrogen iodide under milder conditions than can the conventional processes. For example, acetic acid can be formed from methanol; propionic acid, from ethanol; butyric acid, from propanol; ethyl propionate, from diethyl ether; and phenyl acetate, from anisole. Moreover, since water is not present in the reaction system, the process has a further advantage that substantially anhydrous carboxylic acids can be obtained and a separating operation such as distillation is not required.

The following examples illustrate the present invention more specifically.

EXAMPLES 1 TO 15 AND COMPARATIVE EXAMPLE

A reactor was charged with each of the main catalysts, promotors, solvents, raw materials and organic accelerating agents (as an optional ingredient) indicated in Table 1 in the amounts indicated. Carbon monoxide (or a mixture of carbon monoxide and hydrogen) was introduced under a given pressure, and the reaction was carried out. The reaction conditions and the yields of the products obtained by an analysis of the reaction products are shown in Table 2. The half period is the time required for 50% of the starting alcohol or ether to be converted into the carboxylic acid or its ester.

In Example 13, the starting methanol was continuously fed over 4 hours.

In Examples 1 to 15, water and hydrogen iodide did not substantially form. But in Comparative Example, large quantities of water and hydrogen iodide formed as by-products and provided a corrosive atmosphere.

Table 1

| Example | Starting material (g) | Solvent (g) | Catalyst Main catalyst (g) | Promotor (g) | Organic accelerator (g) |
|---|---|---|---|---|---|
| 1 | Methanol (16) | Phenyl acetate (81.6) | RhCl$_3$ . 3H$_2$O (0.333) | CH$_3$I (14.2) | — |
| 2 | Methanol (16) | Phenyl acetate (81.6) | RhCl(CO) (P$\phi_3$)$_2$ (1.0) | CH$_3$I (14.2) | — |
| 3 | Methanol (16) | Phenyl acetate (81.6) Acetic acid (24) | RhCl$_3$ . 3H$_2$O (0.338) | CaI$_2$. 6H$_2$O (14.7) | P$\phi_3$ (0.7) |
| 4 | Methanol (16) | Phenyl acetate (81.6) Acetic acid (48) | Palladium chloride (0.9) | Calcium iodide (29.4) | P$\phi_3$ (2.9) |
| 5 | Methanol (16) | Phenyl acetate (81.6) | Iridium chloride (0.5) | CH$_3$I (14.2) | P$\phi_3$ (1.8) |
| 6 | Propanol (30) | Phenyl acetate (90.0) Butyric acid (70.4) | H$_2$Pt Cl$_6$ . 6H$_2$O (0.5) | Calcium iodide (29.4) | P$\phi_3$ (1.0) |
| 7 | Methanol (16) | Phenyl acetate (81.6) | RuCl$_3$ . 3H$_2$O (0.5) | CH$_3$I (14.2) | P$\phi_3$ (1.0) |
| 8 | Propanol (30) | Phenyl butyrate (90) Butyric acid (70.4) | Osmium chloride (0.5) | Calcium iodide (29.4) | P$\phi_3$ (1.8) |
| 9 | Methanol (16) | Phenyl acetate (81.6) | Cobalt bromide (2.5) | CH$_3$I (35.5) | P$\phi_3$ (12) |
| 10 | Methanol (16) | Phenyl acetate (81.6) | Iron carbonyl (0.8) | CH$_3$I (35.5) | Triethylamine (1.7) |
| 11 | Ethanol (23) | Phenyl propionate (90) | RhCl$_3$ . 3H$_2$O (0.335) | C$_2$H$_5$I (39) | Diethylamine (0.8) |
| 12 | Diethyl ether (37) Ethanol (11.5) | Tolyl propionate (123) | RhCl$_3$ . 3H$_2$O (0.332) | C$_2$H$_5$I (39) | Tri-n-butyl-amine (1) |
| 13 | Methanol (67.4) | Phenyl acetate (68) | RhCl(CO) (P$\phi_3$)$_2$ (1) | CH$_3$I (14.2) | — |
| 14 | Anisole (50) | Phenyl acetate (50) | RhCl$_3$ . 3H$_2$O (0.1) | CH$_3$I (16) | P$\phi_3$ (1) |
| 15 | Methanol (25.6) | p-Chlorophenyl-acetate (145) | Nichel acetyl-acetonate (2.57) | CH$_3$I (35.5) | P$\phi_3$ (5.8) |
| Comparative Example | Methanol (32) | Acetic acid (72) | RhCl$_3$ . 3H$_2$O (0.333) | CH$_3$I (14.2) | — |

Table 2

| Example | Reaction conditions Temperature (°C.) | Total pressure (kg/cm$^2$ . G) | Partial pressure of CC (kg/cm$^2$G) | Half period (minutes) | Amount of product yielded (g/%) |
|---|---|---|---|---|---|
| 1 | 185 | 38 | 30 | 100 | Acetic acid (28.8/96) |
| 2 | 180 | 41 | 30 | 25 | Acetic acid (29.1/97.0) |
| 3 | 180 | 37 | 30 | 33 | Acetic acid (53.0/96.7) |
| 4 | 200 | 40 | 30 | | Acetic acid (76.8/96.0) |
| 5 | 180 | 40 | 30 | 200 | Acetic acid (28.6/95.3) |
| 6 | 180 | 150 | 140 | | Butyric acid (76.1/13.0) |
| 7 | 180 | 40 | 30 | 240 | Acetic acid (27.3/91.0) |
| 8 | 180 | 152 | 140 | | Butyric acid (74.1/8.4) |
| 9 | 190 | 192 | 170 (10*) | | Acetic acid (23.6/78.7) |
| 10 | 195 | 163 | 150 | | Acetic acid (21.9/73.0) |
| 11 | 180 | 35 | 30 | 110 | Propionic acid |

Table 2-continued

| Example | Reaction conditions | | | Half period (minutes) | Amount of product yielded (g/%) |
|---|---|---|---|---|---|
| | Temperature (°C.) | Total pressure (kg/cm². G) | Partial pressure of CC (kg/cm²G) | | |
| 12 | 190 | 41 | 30 | | (33.5/90.5) Ethyl propionate (46.5/91.2) Propionic acid (16.6/89.6) |
| 13 | 190 | 20 | 17 | | Acetic acid (123.2/97.5) |
| 14 | 195 | 45 | 40 | 61 | Phenyl acetate (108.2/92.4) |
| 15 | 200 | 45 | 30 | 142 | Acetic acid (45.0/93.8) |
| Comparative Example | 180 | 42 | 30 | | Acetic acid (80.9) Water (7.0) Methyl acetate (28.5) hydrogen iodide (4.6) |

*The partial pressure of H₂.

What is claimed is:

1. In a process for producing a carboxylic acid or its ester by reacting an alcohol or an ether with carbon monoxide in the presence of a catalyst composed of at least one metal of Group VIII of the periodic table and a promoter composed of at least one iodine-containing substance selected from the group consisting of iodine and iodine compounds, said alcohol being an aliphatic alcohol containing 1 to 20 carbon atoms, or an aromatic alcohol containing 7 to 20 carbon atoms and said ether being an aliphatic ether containing 2 to 30 carbon atoms or an aromatic ether containing 7 to 30 carbon atoms, the improvement wherein the reaction is performed in the presence of, as a solvent phenyl formate, phenyl acetate, phenyl propionate, phenyl butyrate, phenyl valerate, tolyl acetate, xylyl acetate, mesityl acetate, cumenyl acetate, ethyl phenyl acetate, propyl phenyl acetate, butyl phenyl acetate, chlorophenyl acetate, nitrophenyl acetate, nitrosophenyl acetate, aminophenyl acetate, cyanophenyl acetate,

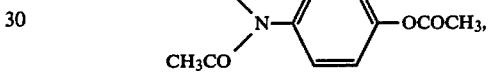

diacetoxybenzene, naphthyl acetate, naphthyl propionate, naphthyl butyrate, diacetoxynaphthalene, diacetoxyanthracene, (diacetoxy)methylanthracene, (diacetoxy)ethylanthracene or (diacetoxy)amylanthracene.

2. The process of claim 1 wherein the reaction is performed in the further presence of an organic accelerating agent composed of an organic compound of a trivalent nitrogen-group element.

* * * * *

UNITED STATES PATENT AND TRADEMARK OFFICE
CERTIFICATE OF CORRECTION

PATENT NO. : 4,212,989
DATED : July 15, 1980
INVENTOR(S) : Tomiya ISSHIKI, Yasuhiko KIJIMA, and Yuh MIYAUCHI It is certified that error appears in the above-identified patent and that said Letters Patent are hereby corrected as shown below:

Please correct the "[30] Foreign Application Priority Data" as follows:

Change "52-131140" to -- 52-131149 --.

Signed and Sealed this

Second Day of June 1981

[SEAL]

Attest:

RENE D. TEGTMEYER

Attesting Officer

Acting Commissioner of Patents and Trademarks